United States Patent
Nguyen

(10) Patent No.: US 6,639,058 B2
(45) Date of Patent: Oct. 28, 2003

(54) METHOD OF DISSOLVING PREFORMED β-AMYLOID PEPTIDE FIBRILS IN VITRO BY POLY-LYSINE

(75) Inventor: Khue Vu Nguyen, San Diego, CA (US)

(73) Assignee: Mai Dao, San Jose, CA (US)

( * ) Notice: Subject to any disclaimer, the term of this patent is extended or adjusted under 35 U.S.C. 154(b) by 0 days.

(21) Appl. No.: 09/848,667

(22) Filed: May 4, 2001

(65) Prior Publication Data

US 2002/0165124 A1 Nov. 7, 2002

(51) Int. Cl.$^7$ .......................... C08H 1/00; A61K 38/02
(52) U.S. Cl. ............................ 530/402; 514/2
(58) Field of Search ................. 514/2, 14; 530/402

(56) References Cited

PUBLICATIONS

Soto et al, Inhibition of Alzheimer's amyloidosis by peptides that prevent beta–sheet conformation. Biochem. Biophys. Res. Commun. 226:672–680, 1996.*

Schenk et al, Immunization with amyloid–beta attenuates Alzheimer disease–like pathology in the PDAPP mouse. Nature, 400:173–177, 1999.*

Bard et al, peripherally administered antibodies against amyloid beta–peptide enter the central nervous system and reduce pathology in a mouse model of alzheimer disease. Nature Medicine, 6:916–919, 2000.*

\* cited by examiner

*Primary Examiner*—Elizabeth Kemmerer
*Assistant Examiner*—Ruixiang Li

(57) ABSTRACT

Beta-amyloid peptide (βA) is a major fibrillar component of neuritic plaques in Alzheimer's disease (AD) brains and is related to the pathogenesis of the disease. The present invention provides a method using Poly-L-Lysine to dissolve preformed βA fibrils in vitro. Its efficiency is instantaneous. Poly-L-Lysine offers the simplest and most effective way to dissolve preformed βA fibrils. The method of this present invention can be used as a universal dissolver of all types of oligomeric β-sheet conformation, precursor of the fibrils. Poly-L-Lysine may also be useful as a future universal therapeutic agent to prevent and/or retard amyloidogenesis in vivo AD and other types of amyloid related disorders.

1 Claim, 2 Drawing Sheets

(a) (b)

METHOD OF DISSOLVING PREFORMED β-AMYLOID PEPTIDE FIBRILS IN VITRO BY POLY-LYSINE

I—FIELD OF THE INVENTION

Figure 1:
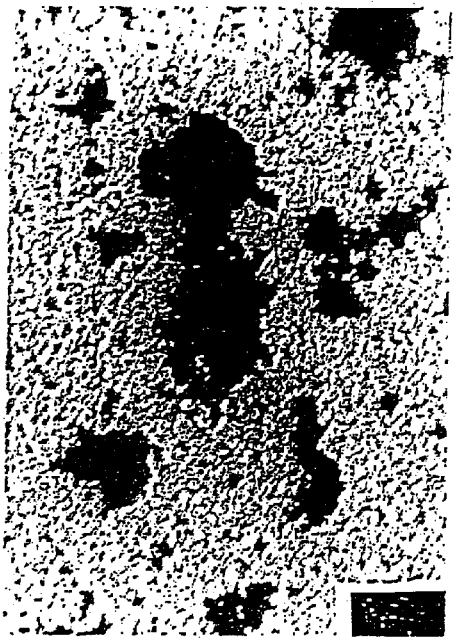
Figure 1:
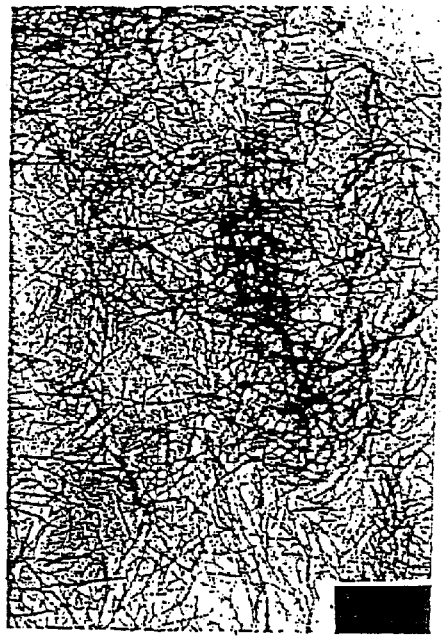

Beta-amyloid peptide (βA) is a major fibrillar component of neuritic plaques in Alzheimer's disease (AD) brains and is related to the pathogenesis of the disease. The present invention concerns the discovery of the efficiency of Poly-L-Lysine to dissolve preformed βA fibrils in vitro. Poly-L-Lysine can be used as a universal dissolver of all types of oligomeric β-sheet conformation, precursor of the fibrils, and it may also serve to prevent and/or retard amyloidogenesis in vivo AD and other types of amyloid related disorders.

II—BACKGROUND OF THE INVENTION

Alzheimer's disease (AD) is a progressive neurodegenerative disease of the elderly, characterized by memory loss and dementia. It is the most frequent cause of dementia in the elderly, accounting for more than 15 million cases worldwide. It is pathologically characterized by proteinaceous deposits in various areas of the brain, particularly in the hippocampus and cerebral cortex (1). Such deposits include extracellular amyloid plaques, composed principally of beta-amyloid (βA), and intracellular neurofibrillary tangles comprising tau protein filaments.

The βA, a 4-kDa peptide of 39–43 amino acids, is a metabolic product of a large transmembrane amino acid precursor molecule, the amyloid precursor protein (APP). APP has several isoforms generated by alternative splicing of a pre-mRNA transcribed from a single 19-exon gene located on the long arm of chromosome 21. The major transcripts are APP695, APP751 and APP770 (2,3). Certain cases of inherited AD have been shown to result from mutations in amyloid precursor protein that lead to enhanced cellular production of the amyloidotic $βA_{1-42}$ peptide which is less soluble and more amyloidogenic than the more common 40-amino acid species. The process of soluble amyloid aggregation into insoluble fibrils is associated with neurotoxicity (4–6), although it is not entirely clear how this is mediated. Furthermore, quantitative histopathology has determined that more than 80% of amyloid plaques are associated with clusters of reactive microglia. As the principal immune effector cells of the brain, activated microglia are capable of releasing cytotoxic agents such as proteolytic enzymes, cytokines, complement proteins, reactive oxygen intermediates, and nitric oxide (7,8). Then, an overabundance of βA and its accumulation as amyloid fibrils trigger disease pathology. This premise has been strengthened greatly by recent studies showing that mutations in the presenilin proteins, which result in familial early-onset AD (9,10), cause increased production of $βA_{1-42}$ (11,12). Recently, transgenic mice overexpressing the $Lys^{670}$-Asn, $Met^{671}$-Leu double mutation in the APP gene have been shown to have age-related AD-like cognitive changes, amyloid plaques, raised levels of the 40-amino acid form of β-amyloid and even greater elevations of the 42/43 amino acid form of β-amyloid (13). Thus, these experiments not only provide convincing evidence that APP abnormalities can cause AD, but also have established an important resource for the exploration of therapeutic and preventing strategies.

Approaches against amyloid plaques under investigation by several laboratories are by way of identifying compounds that can dissolve preformed βA fibrils (14) and, recently, by way of immunizing with βA (15–17). In this study, we demonstrated that the Poly-L-Lysine is a potent dissolver of preformed βA fibrils in vitro.

III—PURPOSE OF THE INVENTION

The object of the present invention is to identify compounds that can dissolve preformed βA fibrils in vitro. Compounds effective as dissolvers of preformed βA fibrils could serve as potential therapeutic agents in the future for the treatment of AD. For such a purpose, hydrosoluble and biocompatible polymers such as Poly-L-Lysine and Polyethylene glycol were used.

IV—DESCRIPTION OF THE INVENTION

In this study, electron microscopy was used to analyse the structure of βA and to evaluate the efficency of compounds to dissolve preformed βA fibrils.

IV—(1) MATERIALS AND METHODS

Reagents $βA_{25-35}$, $βA_{1-40}$, and $βA_{1-42}$, Poly-L-Lysine, hydrobomide (Av. Mol. Wt: 141,000), L-Lysine, monohydrochloride, and phosphotungstic acid, sodium salt, were supplied by Sigma Chemical Co. (St. Louis, Mo.). Polyethylene glycol (Av. Mol. Wt: 6,000) was from Merck (Darmstadt, Germany). All other chemicals used were of reagent grade. Phosphate buffered saline (PBS) was 25 mM in phosphate and 50 mM NaCl, pH 7.2. Deionized and sterilized water was used for the preparation of all solutions.

Sample Preparation

Aliquots of βA at a concentration of 1.5 mg/ml for both $βA_{1-40}$ and $βA_{1-42}$ and 0.5 mg/ml for $βA_{25-35}$ prepared in water or in PBS, were incubated for 5 days at 37° C. At the end of the incubation period, 10 µl of βA solution were mixed with 10 µl of water for negative-staining electron microscopy analysis.

All compounds used to test the ability to dissolve preformed βA fibrils in vitro: Poly-L-Lysine, Polyethylene glycol and L-Lysine, were prepared in water and at a concentration of 25 mg/ml, 10 mg/ml and 1 M respectively. Then, 10 µl of tested compound were mixed with 10 µl of water for negative-staining electron microscopy analysis.

In order to evaluate the ability of compounds to dissolve preformed βA fibrils in vitro, 10 µl of tested compound were mixed with 10 µl of preformed βA fibrils and the negative-staining electron microscopy analysis was immediately performed.

Electron Microscopy

Samples of tested compound, βA with or without tested compound were placed on carbon formar-coated 200-mesh nickel grids. The grids were stained for 5 minutes with 1% phosphotungstic acid and visualized on a Philips EM 401 electron microscope at 80 kV.

IV—(2) Results and Discussion

After 5 days of incubation at 37° C., $βA_{1-40}$ prepared in PBS formed amorphous aggregates (FIG. 1a) whereas fibrillar aggregates were obtained with $βA_{1-40}$ prepared in water (FIG. 1b). Peptides containing the sequence 1–40 or 1–42 of βA and shorter derivatives can form amyloid-like fibrils in the absence of other proteins (18), indicating that the potential to form amyloid resides mainly in the structure of βA. The relation between the primary structure of βA and its ability to form amyloid-like fibrils has been analysed by altering the sequence of the peptide. Substitution of hydrophilic for hydrophobic residues in the βA hydrophobic region (amino acids 17 to 21) impaired fibril formation (19), suggesting that βA assembly is partially driven by hydrophobic interaction. The conformation adopted by βA peptides seems to be an important factor in amyloid formation. βA incubated at different pH, peptide concentration, and solvents, can adopt an α-helical-random coil or a β-sheet secondary structure (20–22). The βA peptide with α-helical or random coil structure aggregates slowly while βA with β-sheet conformation aggregates rapidly (21, 23–25). It seems likely that hydrophobicity facilitates monomeric interaction and that β-sheet content drives this interaction to β-sheet oligomers and amyloid fibrils. Compounds effective as dissolvers of preformed βA fibrils could serve as potential therapeutic agents in the future for the treatment of AD. The Polyethylene glycol, Poly-L-Lysine, and L-Lysine were used to test its potential to dissolve preformed βA fibrils in vitro. As shown in FIG. 2d, preformed $\beta A_{25-35}$ fibrils (the biologically active domain of the βA for neurotrophic and neurotoxic effects located in the $\beta A_{25-35}$ sequence), were completely dissolved in the presence of Poly-L-Lysine. However, its monomer, L-Lysine, and the Polyethylene glycol, were not effective (FIG. 2e and FIG. 2f). It is likely that excess of Poly-L-Lysine may come in between the monomers by means of hydrogen and hydrophobic bonds in the β-sheet secondary structure of the preformed βA fibrils, and therefore blocks the interaction between the monomers in the β-sheet conformation which results in the disassembly of preformed βA fibrils. By comparison with Poly-L-Lysine, the Polyethylene glycol do not have the potential to bind to monomeric βA peptides. This is probably due to the lack of hydrogen bonds. The monomer, L-Lysine, can bind to monomeric βA peptides but this binding, due to its small size, is not effective by itself to block the interaction between monomers in the β-sheet conformation. The disassembly of preformed βA fibrils induced by Poly-L-Lysine may indicate that the monomeric peptide is in equilibrium with the fibrils, as previously suggested (26,27). An excess of Poly-L-Lysine may bind to monomeric peptide thus displacing the equilibrium, and leading to fibril disaggregation. The small size of the monomer, L-Lysine, was not effective to displace the equilibrium. It is important to note that the physical-chemical properties of polymers are frequently very different from those of monomers. The potential of Poly-L-Lysine to dissolve preformed βA fibrils in vitro was also observed with preformed $\beta A_{1-40}$ and $\beta A_{1-42}$ fibrils (data not shown).

Soto et al. (14) have developed an 11-amino acid peptide partially homologous to the central hydrophobic region of βA (amino acids 17 to 21), called inhibitor of βA fibrillogenesis or anti-β-sheet peptide. However, preformed βA fibrils were not completely dissolved even after two days of incubation with this anti-β-sheet peptide (14). Attacking existing amyloid plaques in the brain by immunization with βA (15–17) could subject patients to risks. Indeed, the protein precursor to βA is found in many cell types; therefore, immunization might induce a harmful autoimmune response in nonbrain tissues.

The two problems associated with peptides therapy, namely, transport across the blood-brain barrier and the generation of an immune response, can be minimized by shortening the polypeptide length of Poly-L-Lysine. Another problem is the high sensitivity of peptides to proteolytic degradation; to resolve this problem both L and D forms of Poly-Lysine can be used.

The results of this study demonstrate that the Poly-L-Lysine is a potent dissolver of preformed βA fibrils in vitro. Its efficiency is instantaneous. Poly-L-Lysine offers the simplest and most effective way to dissolve preformed βA fibrils. It can be used as a universal dissolver of all types of oligomeric β-sheet conformation, precursor of the fibrils, and may also serve to prevent and/or retard amyloidogenesis in vivo AD and other types of amyloid related disorders.

REFERENCES

1-Glenner, G. G.; and Wong, C. W. (1984). Alzheimer's disease and Dow's syndrome: Sharing of a unique cerebrovascular amyloid fibril protein. Biochem. Biophys. Res. Commun. 120, 885–890.

2-Goldgaber, D.; Lerman, M. I.; McBride, O. W.; Saffiotti, U.; and Gajdusek, D. C. (1987). Characterization and chromosomal localization of a cDNA encoding brain amyloid of Alzheimer's disease. Science 235, 877–880.

3-Kang, J.; Lemaire, H. G.; Unterbeck, A. et al. (1987). The precursor of Alzheimer's disease amyloid A4 protein resembles a cell-surface receptor. Nature 325, 733–736.

4-Citron, M.; Oltersdorf, T.; Haass, C. et al. (1992). Mutation of the β-amyloid precursor protein in familial Alzheimer's disease increases β-protein production. Nature 360, 672–674.

5-Cai, X. D.; Golde, T. E.; and Younkin, S. G. (1993). Release of excess amyloid β-protein from a mutant amyloid β-protein precursor. Science 259, 514–516.

6-Suzuki, N.; Cheung, T. T.; Cai, X. D. et al. (1994). An increase percentage of long amyloid β-protein secreted by familial amyloid β-protein precursor (β APP717) mutant. Science 264, 1336–1340.

7-Thery, C.; Chamak, B.; Mallat, M. (1991). Free radical killing of neurons. Eur. J. Neurosci. 3, 1155–1164.

8-Lees, G. J. (1993). Nitric oxide is produced by microglia. J. Neurol. Sci. 114, 119–122.

9-Levy, L. E.; Wasco, W.; Pookaj, P. et al. (1995). Candidate gene for the chromosome 1 familial Alzheimer's disease locus. Science 269, 973–977.

10-Sherrington, R.; Rogaev, E. I.; Liang, Y. et al. (1995). Cloning of a gene bearing missense mutations in early-onset familial Alzheimer's disease. Nature 375, 754–760.

11-Duff, K.; Eckman, C.; Zehr, C. et al. (1996). Increased amyloid β42(43) in brains of mice expressing mutant presenilin 1. Nature 383, 710–713.

12-Scheuner, D.; Eckman, C.; Jensen, M. et al. (1996). Secreted amyloid β-protein similar to that in the senile plaques of Alzheimer's disease is increased in vivo by the presenilin 1 and 2 and APP mutations linked to familial Alzheimer's disease. Nat. Med. 2, 864–870.

13-Hsiao, K.; Chapman, P.; Nilsen, S.; Eckman, C.; Harigaya, Y.; Younkin, S.; Yang, F.; and Cole, G. (1996). Correlative memory deficits. Aβ elevation, and amyloid plaques in transgenic mice. Science 274, 99–102.

14-Soto, C.; Mark, S. K.; Marc, B.; and Blas, F. (1996). Inhibition of Alzheimer's amyloidois of peptides that prevent β-sheet conformation. Biochem. Biophys. Res. Comm. 226, 672–680.

15-Schenk, D.; Barbour, R.; Dunn, W.; et al. (1999). Immunization with amyloid-beta attenuates Alzheimer-disease-like pathology in the PDAPP mouse. Nature 400, 173–177.

16-Bard, F.; Cannon, C.; Barbour, R.; et al. (2000). Peripherally administered antibodies against amyloid β-peptide enter the central nervous system and reduce pathology in a mouse model of Alzheimer disease. Nat. Med. 6, 916–919.

17-Schenk, D.; Seubert, P.; Lieberburg, I.; Wallace, J. (2000a). β-peptide immunization. A possible new treatment for Alzheimer disease. Arch. Neurol. 57, 934–936.

18-Soto, C.; Branes, M. C.; Alvarez, J.; Inestrosa, N. C. (1994). Strutural determinants of Alzheimer's amyloid beta-peptide. J. Neurochem. 63, 1191–1198.

19-Hilbich, C.; Kisters-Woike, B.; Reed, J.; Masters, C. L.; Beyreuther, K. (1992). Substitutions of hydrophobic amino acids reduce the amyloidogenicity of Alzheimer's disease beta A4 peptides. J. Mol. Biol. 228, 460–473.

20-Barrow, C. J.; Yasuda, A.; Kenny, P. T.; Zagorski, M. G. (1992). Solution conformations and aggregational properties of synthetic amyloid beta-peptides of Alzheimer's disease. Analysis of circular dichroism spectra. J. Mol. Biol. 225, 1075–1093.

21-Burdick, D.; Soreghan, B.; Kwon, M.; Kosmoski, J.; Knauer, M.; Henschen, A.; Yates, J.; Cotman, C.; Glabe, C. (1992). Assembly and aggregation properties of synthetic Alzheimer's A4/beta amyloid peptide analogs. J. Biol. Chem. 267, 546–554.

22-Zagorski, M. G.; Barrow, C. J. (1992). NMR studies of amyloid beta-peptides: Proton assignments, secondary structure, and mechanism of an alpha-helix beta-sheet conversion for a homologous, 28 residue, N-terminal fragment. Biochemistry. 31, 5621–5631.

23-Soto, C.; Castano, E. M.; Frangione, B.; Inestrosa, N. C. (1995). The alpha-helical to beta-strand transition in the amino-terminal fragmer amyloid beta-peptide modulates amyloid formation. J. Biol.Chem. 270, 3063–3067.

24-Soto, C.; Frangione, B. (1995). Two conformational states of amyloid beta-peptide: Implications for the pathogenesis of Alzheimer's disease. Neurosci. Lett. 186, 115–118.

25-Soto, C.; Castano, E. M. (1996). The conformation of Alzheimer's beta peptide determines the rate of amyloid formation and its resistance to proteolysis. Biochem. J. 314, 701–707.

26-Maggio, J. E.; Stimson, E. R.; Ghilardi, J. R.; et al. (1992). Reversible in vitro growth of Alzheimer disease beta-amyloid plaques by deposition of labeled amyloid peptide. Proc. Natl. Acad. Sci. USA. 89, 5462–5466.

27-Tamaoka, A.; Konto, T.; Odaka, A.; Sahara, N.; Sawamura, N.; Ozawa, K.; Suzuki, N.; Shoji, S.; Mori, H. (1994). Biochemical evidence for the long-tail form (A beta 1-42/43) of amyloid beta protein as a seed molecule in cerebral deposits of Alzheimer's disease. Biochem. Biophys. Res. Comm. 205, 834–842.

LEGEND OF FIGURES

FIG. 1: Electron microscopy analysis of the structure of βA.

(a) Amorphous aggregates (b) Fibrillar aggregates

Figure 2:
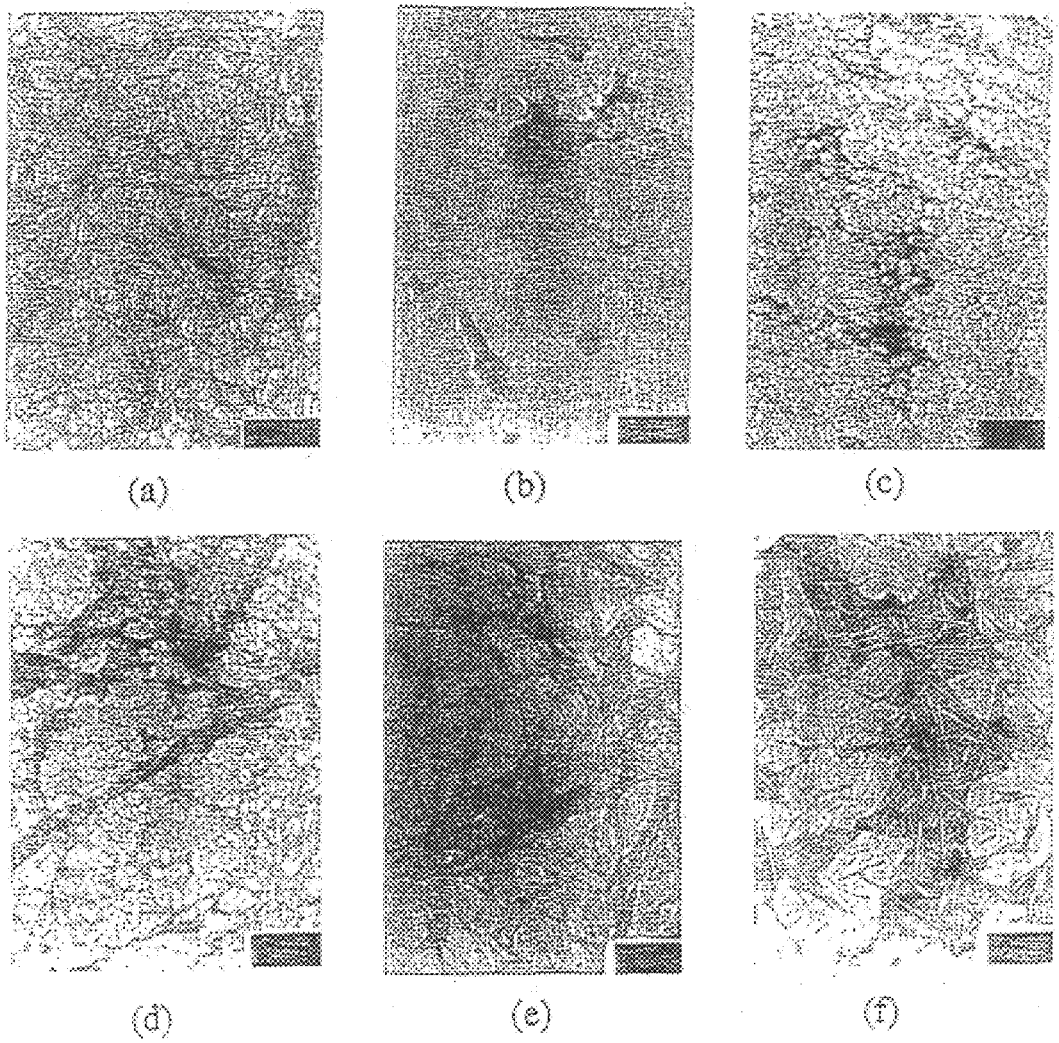

FIG. 2: Electron microscopy analysis of the ability to dissolve preformed βA fibrils in vitro.

(a) Preformed $\beta A_{25-35}$ fibrils (b) Polyethylene glycol (c) Poly-L-Lysine (d) Preformed $\beta A_{25-35}$ fibrils+Poly-L-Lysine (e) Preformed $\beta A_{25-35}$ fibrils+L-Lysine (f) Preformed $\beta A_{25-35}$ fibrils+Polyethylene glycol

What is claimed is:

1. A method of dissolving preformed β-amyloid peptide fibrils in vitro, comprising:

(a) incubating β-amyloid peptides in water or in phosphate buffered saline at 37° C. for 5 days to form β-amyloid peptide fibrils;

(b) contacting the preformed β-amyloid peptide fibrils with poly-L-lysine or poly-D-lysine;

(c) evaluating the dissolving efficiency by negative-staining electron microscopy immediately.

* * * * *